United States Patent
Kurosawa et al.

(10) Patent No.: US 9,625,464 B2
(45) Date of Patent: *Apr. 18, 2017

(54) FLUORESCENT PROBE FOR PLASMA CELL IDENTIFICATION AND ISOLATION, AND PLASMA CELL IDENTIFICATION OR ISOLATION METHOD USING THE PROBE

(75) Inventors: Nobuyuki Kurosawa, Toyama (JP); Masaharu Isobe, Toyama (JP)

(73) Assignee: NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/637,025

(22) PCT Filed: Mar. 22, 2011

(86) PCT No.: PCT/JP2011/056831
§ 371 (c)(1),
(2), (4) Date: Oct. 18, 2012

(87) PCT Pub. No.: WO2011/118579
PCT Pub. Date: Sep. 29, 2011

(65) Prior Publication Data
US 2013/0029325 A1    Jan. 31, 2013

(30) Foreign Application Priority Data
Mar. 25, 2010  (JP) .................................. 2010-070730

(51) Int. Cl.
G01N 33/58    (2006.01)
G01N 33/569    (2006.01)

(52) U.S. Cl.
CPC ..... *G01N 33/582* (2013.01); *G01N 33/56966* (2013.01)

(58) Field of Classification Search
None
See application file for complete search history.

(56) References Cited

U.S. PATENT DOCUMENTS

2011/0231960 A1    9/2011    Sawada et al.

FOREIGN PATENT DOCUMENTS

| JP | 2005511021 A | 4/2005 |
|---|---|---|
| JP | 2008022776 A | 2/2008 |
| WO | WO 00/79274 | 12/2000 |
| WO | 03025542 A2 | 3/2003 |
| WO | WO 2004/051268 | 6/2004 |
| WO | 2009133882 A1 | 11/2009 |

OTHER PUBLICATIONS

Kirk et al, Biogenesis of secretory organelles during B cell differentiation, Journal of Leukocyte Biology, vol. 87, Feb. 2010.*
Sacco, The Mononuclear Phagocyte System and Lymphocytes, Ultrastructural Pathlogy the comparative Cellular Basis of Disease, Second Edition, 2009.*
ER-Tracker, ER-Tracker Dyes for Live-Cell Endoplasmic Reticulum Labeling, Molecular Probes Catalog, 2005.*
SYTO-Dyes, SYTO Nucleic Acid Stains, Molecular Probes Catalog, Aug. 2003.*
Wols, Plasma Cells, Encyclopedia of Life Sciences, 2005.*
Manz et al, Lifetime of plasma cells in the bone marrow, Nature, vol. 388, 1997.*
Fooksman, Development and Migration of Pre-Plasma Cells in the Mouse Lymph Node, Immunity, 2010, 33(1): 118-127.*
Syto® Red Fluorescent Nucleic Acid Stains. [online]. Molecular Probes product Information. Jan. 15, 2001. [Retrieved on Jun. 8, 2011]. Retrieved from the internet: <URL:http://probes.invitrogen.com/media/pis/mp11340.pdf>.
Sanderson et al., "B lymphocytes express and lose syndecan at specific stages of differentiation" Cell Regulation, Nov. 1989, pp. 27-35, vol. 1.
Horst et al., "Detection and characterization of plasma cells in peripheral blood: correlation of IgE+ plasma cell frequency with IgE serum titre", Clin Exp Immunol, 130, (2002), pp. 370-378.
International Search Report for corresponding International Application No. PCT/JP2011/056831, Jun. 21, 2011.
International Preliminary Report on Patentability with Written Opinion of the International Searching Authority for corresponding International Application No. PCT/JP2011/056831, Oct. 11, 2012.
L. Cole et al., "ER-Tracker dye and BODIPY-brefeldin A differentiate the endoplasmic reticulum and Golgi bodies from the tubular-vacuole system in living hyphae of Pisolithus tinctorius", Journal of Microscopy, Mar. 2000, pp. 239-248, vol. 197,pt 3.
Chinese Office Action for corresponding CN Application No. 201180015816.6, Jul. 25, 2013.

(Continued)

*Primary Examiner* — Taeyoon Kim
*Assistant Examiner* — Srikanth Patury
(74) *Attorney, Agent, or Firm* — Ditthavong & Steiner, P.C.

(57) ABSTRACT

A method which can isolate plasma cells and plasmablasts efficiently and with high purity, from mammals and birds, without using a cell surface marker is provided.
Further disclosed is a fluorescent probe wherein the staining selectivity for the endoplasmic reticulum of cells is higher than the staining selectivity for cell organelles other than the endoplasmic reticulum. Also disclosed is a method for identifying plasma cells and plasmablasts which includes staining cells derived from lymph node tissue or similar by using this probe, and identifying plasma cells and plasmablasts on the basis of the fluorescence intensity from the stained cells. Also disclosed is a fluorescent probe wherein the staining selectivity for cell nuclei is higher than the staining selectivity for cell organelles other than the cell nuclei. Also disclosed is a method for identifying plasma cells and plasmablasts in lymph node tissue or similar which includes staining cells derived from lymph node tissue or similar by using this probe, and identifying plasma cells and plasmablasts on the basis of the fluorescence intensity from the stained cells.

10 Claims, 2 Drawing Sheets

(56) References Cited

OTHER PUBLICATIONS

Chinese Office Action for corresponding CN Application No. 201180015816.6, Feb. 11, 2014.
European Office Action for corresponding EP Application No. 11 759 384.8-1408, Jan. 28, 2014.
Kurosawa et al., "Rapid production of antigen-specific monoclonal antibodies from a variety of animals", BMC Biology, Biomed central, Sep. 28, 2012, p. 80, vol. 10, No. 1, XP021129263.
Extended European Search Report for corresponding EP Application No. 11759384.8-1408, Jul. 26, 2013.
Deng et al., "Fluorescent conjugates of brefeldin a selectively stain the endoplasmic reticulum and Golgi complex of living cells", Journal of Histochemistry and Cytochemistry, 1995, vol. 43, No. 9, pp. 907-915.
Takemoto, "Ultrastructural and immunohistochemical observations of plasma cells of the human labial glands", with English Abstract, Kawasaki Ikai-shi, 1997, vol. 23, No. 2, pp. 87-97.
Tsutsumi, "Plasma Cell—Who on earth are you?", Microscopia, vol. 12, No. 3, 1995, pp. 2-9.
Summons to Attend Oral Proceedings Pursuant to Rule 115(1) EPC in the corresponding European patent application, European Patent Application Serial No. 1175934.8, 4 pages.
Japanese Office Action for related Japanese Patent Application No. 2012-507008 dated Feb. 24, 2015, 10 Pages.
"Probe for endoplasmic reticulum and Golgi body", Chapter 1 Cell Biology and Imaging, Invitrogen 2004-2005 Nenban Catalog, 2004, pp. 1-44 and 1-49.
Murakami et al., "Cell Biological Applications of Fluorescent Probes," Kenbikyo 42: 65-68 (2007), 5 Pages.
Japanese Office Action for related Japanese Patent Application No. 2012-507008 dated Feb. 18, 2015, 10 Pages.

\* cited by examiner

Staining with endoplasmic reticulum affinity fluorescent dye    Staining with FITC labeled anti-guinea pig antibody

FLUORESCENT PROBE FOR PLASMA CELL IDENTIFICATION AND ISOLATION, AND PLASMA CELL IDENTIFICATION OR ISOLATION METHOD USING THE PROBE

CROSS-REFERENCE TO RELATED APPLICATION(S)

This application is based upon and claims the benefits of priority from JP Patent Application 2010-70730, filed on Mar. 25, 2010, the entire disclosure of which is incorporated herein by reference.

TECHNICAL FIELD

The present invention relates to the fluorescent probe for identifying and isolating plasma cells and plasmablasts and the method for identifying or isolating plasma cells and plasmablasts by using the probe.

BACKGROUND ART

An antibody plays important roles in the biophylaxis by specifically binding to a target antigen. Recently, antibody drugs which utilize its specific binding properties against its antigen have been developed as a therapeutic medication for autoimmune diseases or intractable diseases such as cancers, and its utility has high appraisal. In response to the development needs in effective manufacturing techniques for monoclonal antibodies having high specificity and high affinity which become antibody drugs, the techniques for making antigen-specific monoclonal antibodies by using gene cloning methods from human and mouse antibody producing cells have being established in recent years. The methods mainly include the following three steps: (1) isolation of antibody producing cells from peripheral bloods and lymphatic tissues of an immunity formation animal; (2) cloning of immunoglobulin genes from the antibody producing cells; and (3) antibody production by introducing the immunoglobulin genes into host cells. In order to make monoclonal antibodies effectively by using this technique, first of all antibody producing cells must be isolated with high purity. B lymphocyte or its terminally differentiated ones, plasma cells and plasmablasts are generally used as the antibody producing cells.

Plasma cells and plasmablasts are the cells which are terminally differentiated from B lymphocyte and specialized in antibody production. Since somatic mutations of antibody genes and selection with antigen which is called as affinity maturation are executed in these cells, these cells are particularly useful for isolating antibodies having high binding activities. However, because plasma cells and plasmablasts are heterogeneous cell population by consisting of several subsets and those abundance ratio is less 0.1% in lymphatic tissues, its isolation with high purity is difficult. Now, in order to identify and isolate plasma cells or plasmablasts from peripheral blood or lymph node, several steps of positive/negative selection are necessary which employ a combination of antibodies against at least three kinds of cell surface markers (Non Patent Literature 1).

CITATION LIST

Non-Patent Literature

[Non Patent Literature 1] Sanderson, R. D., Lalor, P., Bernfield, M. B lymphocytes express and lose syndecan at specific stages of differentiation: Cell Regulation 1: 27-35 (1989)

[Non Patent Literature 2] Horst, A. Hunzelmann, N. Arce, S. Herber, M. Manz, R. A. Radbruch, A. Nischt, R. Schmitz, J. Assenmacher, M. Clin. Exp. Immunol. 130: 370-378 Detection and characterization of plasma cells in peripheral blood: correlation of IgE+ plasma cell frequency with IgE serum titre (2002)

The entire disclosures of the non patent literatures 1 and 2 are incorporated herein by reference.

SUMMARY OF INVENTION

Technical Problem

Since several steps of positive/negative selection are necessary for identifying and isolating plasma cells or plasmablasts from peripheral blood or lymph node as described above, the identification and isolation of plasma cells or plasmablasts takes time and troublesome.

Moreover, the separation method for plasma cells and plasmablasts by using an antibody against a cell surface marker is only established with mouse and human at present (Non patent literature 1, 2). Therefore, monoclonal antibody production by using gene cloning methods only employs a plasma cells and plasmablasts derived from human and mouse.

However, most of functional antigen epitope of human proteins which are targets for antibody drugs have high homology between human and mouse, and thus, when a mouse is immunized with the protein, it is often difficult to obtain an antibody having high specificity because of immunological tolerance. In order to avoid such limitation based on immunological tolerance, monoclonal antibodies which can be obtained by immunizing animal species other than mouse become more important as a new target of antibody drug developments. Nevertheless, a method for identifying and separating plasma cells and plasmablasts as antibody producing cells from animals such as rabbit, rat, sheep, goat, and fowl has not been established yet because an antibody against antibody producing cell surface marker in these animals has not been made.

Therefore, the purpose of the present invention is to provide the means which can isolate plasma cells and plasmablasts effectively and with high purity without using a cell surface marker, from various animals through mammalian including human and mouse to a bird.

Solution to Problem

Plasma cells and plasmablasts have the distinguishing forms, which are not recognized in other cells, as follows: (1) The endoplasmic reticulum which is the cell organelle participating in translation, folding, and maturation of proteins extraordinarily grows and occupies most of cytoplasm. (2) The cell nuclei are small and maldistributed in one side of cells, and in the nuclei the chromosomes are aggregated and the heterochromatin having car spoke like structure is recognized.

The present inventors thought that these characteristics were the form appeared by that plasma cells and plasmablasts specialized in producing large amount of antibodies and thus by using the form plasma cells and plasmablasts could be isolated in any animal regardless to its species.

Based on the above idea, the present inventors have screened lots of fluorescent probes for selective staining plasma cells and plasmablasts. As a result, the inventors found fluorescent probes which strongly stain plasma cells and plasmablasts but stain other cells possibly co-existing with plasma cells and plasmablasts with lower degree of staining, and provides a distinguishable difference in fluorescent intensity between them (fluorescent probe 1). Furthermore, the inventors found fluorescent probes which strongly stain nuclei of other cells possibly co-existing with plasma cells and plasmablasts but have low affinity to nuclei of plasma cells and plasmablasts (fluorescent probe 2). In addition, the inventors have found that by using these fluorescent probes plasma cells and plasmablasts could be effectively identified from lymph node tissue or blood corpuscle sample without the use of an antibody against a cell surface marker, and furthermore the identified plasma cells and plasmablasts could be isolated, and have made the present invention.

The present invention is as the followings.

[1] A fluorescent probe for identifying or isolating plasma cell(s) and/or plasmablast(s), wherein the staining selectivity for the endoplasmic reticulum in cells is higher than the staining selectivity for cell organelles other than the endoplasmic reticulum, and with the staining of the fluorescent probe, plasma cell(s) and plasmablast(s) are distinguishable from cells other than plasma cells and plasmablasts.

[2] The fluorescent probe described in [1], wherein the fluorescent probe is selected from the group consisting of (1) a substance which is amphiphilic and cationic and have moderate lipophilicity and (2) a substance which has affinity to a protein localized in the endoplasmic reticulum above a certain degree.

[3] The fluorescent probe described in [2], wherein the amphiphilicity is defined by the amphiphilicity index (AI) as +6>AI>0, the moderate lipophilicity is defined by the hydrophobic index (log P) as +6>log P>0, and the affinity above a certain degree is defined by the dissociation constant of the range of 0.1 μM to 0.1 nM.

[4] The fluorescent probe described in any one of [1] to [3], wherein the cell organelle other than the endoplasmic reticulum is plasma-membrane, mitochondria, Golgi body, lysosome, peroxisome, nuclei, centrosome, cytoplasm, phagosome, endosome, or aggresome.

[5] The fluorescent probe described in any one of [1] to [4], wherein the fluorescent probe is selected from the group consisting of fluorescent labeled glibenclamide, fluorescent labeled Brefeldin A, fluorescent probe, and fluorescent protein.

[6] A fluorescent probe for identifying or isolating plasma cell(s) and/or plasmablast(s), wherein the staining selectivity for cell nuclei is higher than the staining selectivity for cell organelles other than cell nuclei, and with the staining of the fluorescent probe, plasma cell(s) and plasmablast(s) are distinguishable from cells other than plasma cells and plasmablasts.

[7] The fluorescent probe described in [6], wherein the fluorescent prove is a substance having affinity to DNA.

[8] The fluorescent probe described in [7], wherein the substance having affinity to DNA is a substance in which two nitrogen atoms are connected via a polymethylene chain, each nitrogen atom independently forms an aromatic ring, and at least one nitrogen atom has positive electric charge as quaternary ammonium.

[9] The fluorescent probe described in [8], wherein the substance has the amphiphilicity index (AI) of <8, and the hydrophobic index (log P) of −5<log P(cation)<0.

[10] The fluorescent probe described in any one of [6] to [9], wherein the fluorescent probe is SYTO (registered trademark) 59 or SYTO (registered trademark) 24.

[11] The fluorescent probe described in any one of [1] to [5], wherein the cells other than plasma cells and plasmablasts are at least one type of cell selected from the group consisting of erythrocyte, platelet, monocyte, basocyte, acidocyte, neutrophil, B lymphocyte, T lymphocyte and macrophage.

[12] The fluorescent probe described in any one of [6] to [10], wherein the cells other than plasma cells and plasmablasts are at least one type of cell selected from the group consisting of monocyte, basocyte, acidocyte, neutrophil, B lymphocyte, T lymphocyte and macrophage.

[13] The fluorescent probe described in any one of [1] to [12], wherein the probe is used for isolating plasma cell(s) and plasmablast(s) from lymph node tissue, hemocyte preparation or bone marrow.

[14] A method for identifying plasma cell(s) and plasmablast(s) in lymph node tissue, hemocyte preparation or bone narrow, comprising:
staining cells derived from lymph node tissue, hemocyte preparation or bone marrow by using the fluorescent probe described in any one of [1] to [5] or a combination thereof, and
identifying plasma cell(s) and/or plasmablast(s), or candidate(s) of plasma cell(s) and/or plasmablast(s) based on fluorescent intensity of the stained cells.

[15] A method for preparing plasma cell(s) and plasmablast(s) comprising harvesting plasma cell(s) and/or plasmablast(s) or candidate(s) of plasma cell(s) and/or plasmablast(s) identified by the method described in [14].

[16] The method described in [15], wherein the harvesting of plasma cell(s) and/or plasmablast(s) or candidate(s) of plasma cell(s) and/or plasmablast(s) is performed by sort of a cell sorter.

[17] A method for identifying plasma cell(s) and plasmablast(s) in lymph node tissue, hemocyte preparation or bone narrow, comprising:
staining cell(s) derived from lymph node tissue, hemocyte preparation or bone marrow by using the fluorescent probe described in any one of [6] to [10] or a combination thereof, and
identifying plasma cell(s) and/or plasmablast(s), or candidate(s) of plasma cell(s) and/or plasmablast(s) based on fluorescent intensity of the stained cell(s).

[18] A method for preparing plasma cell(s) and plasmablast(s) comprising harvesting plasma cell(s) and/or plasmablast(s) or candidate(s) of plasma cell(s) and/or plasmablast(s) identified by the method described in [17].

[19] The method described in [17], wherein the harvesting of plasma cell(s) and/or plasmablast(s) or candidate(s) of plasma cell(s) and/or plasmablast(s) is performed by sort of a cell sorter.

[20] A method for preparing plasma cell(s) and plasmablast(s) comprising: staining cell(s) which are harvested described in [15] or [16] by using the fluorescent probe described in any one of [6] to [10] or a combination thereof,
identifying cell(s) other than plasma cells and plasmablasts, or candidate(s) of cell(s) other than plasma cells and plasmablasts based on fluorescent intensity of the stained cell(s),
harvesting cell(s) identified, and
harvesting the remaining cell(s) as plasma cell(s) and/or plasmablast(s), or candidate(s) of plasma cell(s) and/or plasmablast(s).

[21] The method described in [20], wherein the harvesting of cell(s) other than plasma cells and plasmablasts or candidate(s) of cell(s) other than plasma cells and plasmablasts and the harvesting of the remaining cell(s) are performed by sort of a cell sorter.

[22] The method described in any one of [13] to [21], wherein the lymph node tissue, hemocyte or bone marrow is derived from human, anthropoid, monkey, canine, cat, horse, bovine, porcine, sheep, caprine, donkey, camel, lama, alpaca, reindeer, buffalo, yak, guinea pig, rabbit, mink, mouse, rat, Mongolian gerbil, hamster, golden hamster, Armenian hamster, ferret, miniature pig, raccoon, opossum, suncus, kangaroo, dolphin, fowl, quail or ostrich.

Advantageous Effect of Invention

According to the present invention plasma cells and plasmablasts can be identified with paying attention to the staining selectivity of the fluorescent probe(s) for cell organelles and so on without using an antibody against a cell surface marker. Therefore, an antibody itself against a cell surface marker is unnecessary for identifying plasma cells and plasmablasts, and it is possible to identify and isolate plasma cells and plasmablasts without limiting to particular animal species. Therefore, according to the present invention it is possible to make monoclonal antibodies without depending on specific animal species. At present, only human and mouse antibodies have been used for developing antibody drugs, but with using the present invention it is possible to utilize monoclonal antibodies obtained from lots of animal species for developing antibody drugs. Thus, the present invention provides new and prevailing technique for developing antibody drugs which is predominant in the development of new drugs.

DESCRIPTION OF EMBODIMENTS

Fluorescent Probe 1

Figure 1:
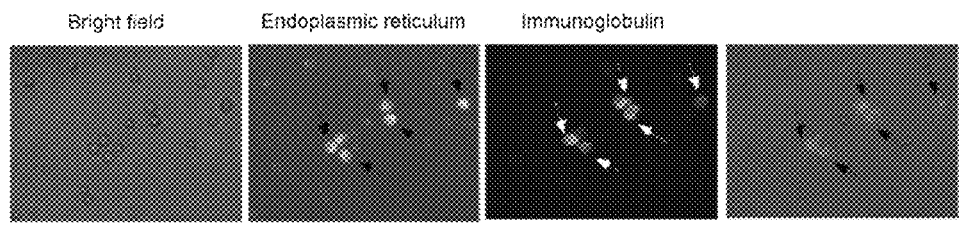
FIG. 1 shows the result of identification test of plasma cells and plasmablasts with the fluorescent probe which selectively stains the endoplasmic reticulum in Example 1. The result is the fluorescent microscope observation of the cell group of CD49b negative, CD45R negative and CD138 positive by staining with ER-Tracker (registered trademark) Blue-White DPX/lipid.

The fluorescent probe (fluorescent probe 1) as the first embodiment of the present invention is the fluorescent probe to use for identifying and isolating plasma cells and plasmablasts and has affinity to the cell endoplasmic reticulum higher than to other organelles. In other words, it is the fluorescent probe which selectively stains the cell endoplasmic reticulum. Plasma cells and plasmablasts have the abnormally developed endoplasmic reticulum compared to cells other than plasma cells and plasmablasts, and which results in that the fluorescent intensity obtained by the staining with the fluorescent probe 1 gives the identifiable difference between plasma cells and plasmablasts and cells other than a plasma cells and plasmablasts, compared to the fluorescent intensity of cells other than plasma cells and plasmablasts stained with the fluorescent probe 1. The fluorescent intensity ratio (the fluorescent intensity of plasma cells and plasmablasts/the intensity of cells other than plasma cells and plasmablasts) obtained with the fluorescent probe 1 shows, for example, equal to or more than three times.

There is not a big difference for the affinity to the fluorescent probe 1 between the endoplasmic reticulum of plasma cells and plasmablasts and one of cells other than plasma cells and plasmablasts, but the difference in the development of the endoplasmic reticulum of those cells results in the difference in the fluorescent intensity. As a result, based on the fluorescent intensity ratio with the staining of the fluorescent probe 1, plasma cells and plasmablasts can be discriminated from cells other than plasma cells and plasmablasts.

By staining with the fluorescent probe 1, plasma cells and plasmablasts and cells other than plasma cells and plasmablasts co-existing with them can be discriminated each other by the difference in strong and weak between the fluorescent intensity of plasma cells and plasmablasts and the fluorescent intensity of cells other than plasma cells and plasmablasts. Therefore, by staining with the fluorescent probe 1, plasma cells and plasmablasts can be easily identified among a cell group in which cells other than plasma cells and plasmablasts co-exist, and by harvesting the identified plasma cells and plasmablasts, a cell group having more plasma cells and plasmablasts can be obtained.

When the fluorescent intensity of plasma cells and plasmablasts stained with the fluorescent probe 1 is equal to or more than three times compared to the fluorescent intensity of cells other than plasma cells and plasmablasts, those cells can be discriminated each other, and from the view point of achieving more easier discrimination, the ratio is preferably equal to or more than four times and more preferably equal to or more than five times. However, the fluorescent intensity ratio varies depending on cell type of cells other than plasma cells and plasmablasts because the development stage of the endoplasmic reticulum varies depending on cell type of cells other than plasma cells and plasmablasts. The higher the fluorescent intensity ratio is, the more efficient plasma cells and plasmablasts can be identified among a cell group including cells other than plasma cells and plasmablasts. As examples of cells other than plasma cells and plasmablasts, for example, erythrocyte, platelet, T lymphocyte, B lymphocyte, granulocyte, macrophage, acidocyte, basocyte, and so on can be listed.

According to the present invention, the discrimination between plasma cells and plasmablasts and cells other than plasma cells and plasmablasts by using the fluorescent probe 1 of the present invention can be accomplished as below. The fluorescent probe 1 is added to cell suspension and the resulting solution is incubated at 37° C. for 30 min for staining. A suitable concentration of the fluorescent probe 1 for staining depends on the kind of the fluorescent probe 1, and, for example, it is the range of 100 nM to 1 μM. After staining, cells are washed with PBS. Washed cells are subject to, for example, (1) observing the localization of the fluorescent probe in cells by using a fluorescent microscope, or (2) based on the intensity of fluorescence emitting from cells, the cells can be identified as plasma cells and plasmablasts or cells other than plasma cells and plasmablasts. The way of discriminating between plasma cells and plasmablasts and cells other than plasma cells and plasmablasts will be described in detail in the method for identifying and isolating plasma cells and plasmablasts.

Moreover, with applying the method for discriminating plasma cells and plasmablasts and cells other than plasma cells and plasmablasts, a substance which can be used as the fluorescent probe 1 can be screened from substances having unknown staining selectivity for the endoplasmic reticulum of plasma cells and plasmablasts and the endoplasmic reticulum of cells other than plasma cells and plasmablasts. The screening for fluorescent probes which are suitable as the fluorescent probe 1 of the present invention and have high staining selectivity for the endoplasmic reticulum in cells is accomplished by using the method for obtaining the ratio (B/A) of the fluorescent intensity B from the endoplasmic reticulum to the fluorescent intensity A from the whole cells, which uses the method for identifying the cell endoplasmic reticulum by immunostaining a protein localizing in the endoplasmic reticulum (immunoglobulin in plasma cells and plasmablasts) or expressing an endoplasmic reticulum-transitional recombinant fluorescent protein in cultured cells, described later.

A method for screening a substance which can be used as the fluorescent probe 1 can be accomplished by using only plasma cells and plasmablasts or only cells other than plasma cells and plasmablasts. In this regard, since plasma cells and plasmablasts have the developed endoplasmic reticulum and high fluorescent intensity can be obtain by staining the cells, it is easier in the evaluation of the staining selectivity of the substance for the cell endoplasmic reticulum when it uses plasma cells and plasmablasts. However, it is not easy to obtain plasma cells and plasmablasts, and thus it can screen a substance which can be used as the fluorescent probe 1 by evaluating staining properties (staining power) for the endoplasmic reticulum by using cells other than plasma cells and plasmablasts. For example, in a staining experiment using a common cultured cells (e.g., Hela cell) it can obtain the fluorescent intensity ratio (B/A) from the fluorescent intensity A of the whole cells and the fluorescent intensity B of the endoplasmic reticulum, and screen a substance which can be used as the florescent probe 1. However, when cells other than plasma cells and plasmablasts are used as cells, it is appropriate to arbitrarily set the B/A value for threshold as a lower value, which is below the B/A value as the threshold used in the screening method using plasma cells and plasmablasts, for example 50% of it, depending on the degree of development of the endoplasmic reticulum in cells.

As an example of the cells other than plasma cells and plasmablasts, erythrocyte, platelet, T lymphocyte, B lymphocyte, macrophage, neutrophil, acidocyte, basocyte and so on can be listed. Moreover, hybridoma cells, plasmacytoma or multiple myeloma cells can also be used for the screening in the above mentioned way instead of plasma cells and plasmablasts. This is why the endoplasmic reticulum in hybridoma cells, plasmacytoma and multiple myeloma cells is also developed to produce immunoglobulin, and thus it results in high fluorescent intensity of staining and it is easier to evaluate the staining selectivity of a substance for the endoplasmic reticulum of cells.

As an example of a substance for the fluorescent probe 1 having high staining selectivity for the endoplasmic reticulum of plasma cells and plasmablasts and cells other than plasma cells and plasmablasts, (1) a substance which is cationic in amphiphilic condition and has moderate lipophilicity, and (2) a substance which has a certain level of affinity to a protein localizing in the endoplasmic reticulum are listed. Such substances having the property of (1) or (2) show higher staining properties for both the endoplasmic reticulum of plasma cells and plasmablasts and the endoplasmic reticulum of cells other than plasma cells and plasmablasts, compared to other organelles in cells.

The term "cationic in amphiphilic condition" of the above (1) means in particular that the amphiphilic index (AI) is, for example, shown as +6>AI>0. However, the amphiphilic index is obtained by calculating the apparent log P value of a lipophilic domain of a molecule. Specifically the value is calculated according to the model of Morrall et al, based on the fragment value of Hansch et al., and by considering the length and position relationship of the carbon chains and the polar effect of the cationic quaternary ammonium group. [Hansch C, Leo A J. *Exploring QSAR: Fundamentals and Applications in Chemistry and Biology*, p. 160, American Chemical Society: Washington, D.C., 1995, Morrall S W, Herzog R R, Kloepper-Sams P, Rosen M J. Octanol/water partitioning of surfactants and its relevance to toxicity and environmental behavior. *Proc 4th World Surfactants Congress*, vol. 3. AEPSAT: Barcelona, 1996; 220-227.]

The term "moderate lipophilicity" of the above (1) means that the hydrophobic index (log P) is, for example, shown as +6>log P>0. The hydrophobic index is the hydrophobic value of the whole molecule calculated by the fragment estimation method of Hansch et al. Specifically, the value is obtained from the hydrophilic group shown as AI by adding the structural effect associated with it.

The term "has a certain level of affinity to a protein localizing in the endoplasmic reticulum" of the above (2) means in particular that it has the affinity shown by the dissociation constant as 0.1 μM-0.1 nM. A substance which has a certain level of affinity to a protein localizing in the endoplasmic reticulum is the fluorescent probe which selectively stains the endoplasmic reticulum in cells (1) As an example of the substance which is cationic in amphiphilic condition and has moderate lipophilicity, the substances shown by the followings A, B and C are listed.

The compound shown by the formula A is DiOC6(3) (3, 3'-dihexyloxacarbocyanine iodide), and accumulates into mitochondria in low concentration but accumulates into the endoplasmic reticulum in high concentration. The compound shown by the formula B is rhodamine B hexyl ester, and accumulates into mitochondria in low concentration but accumulates into the endoplasmic reticulum in high concentration. The compound shown by the formula C is ER-Tracker Blue white DPX, and accumulates mainly in the endoplasmic reticulum but also stains Golgi body in high concentration. Any of the compounds shown by these A, B or C, which were used in the examples, is cationic in amphiphilic condition and has moderate lipophilicity (Referring to the references: Why fluorescent probes for endoplasmic reticulumare selective: an experimental and QSAR-modeling study).

The amphiphilic index (AI) and the hydrophobic index of the compound shown by the formula A is 4.5 and 4.4, respectively, and the compound has an univalent cation. The amphiphilic index (AI) and the hydrophobic index of the compound shown by the formula B is 4.8 and 5.9, respectively, and the compound has an univalent cation. The amphiphilic index (AI) and the hydrophobic index of the compound shown by the formula C is 5.1 and 0.7, respectively, and the compound has an univalent cation. The compound shown by the formula C has the fluorescent intensity of staining plasma cells and plasmablasts which is four times higher or more than the fluorescent intensity of staining cells other than plasma cells and plasmablasts.

[Formula 1]

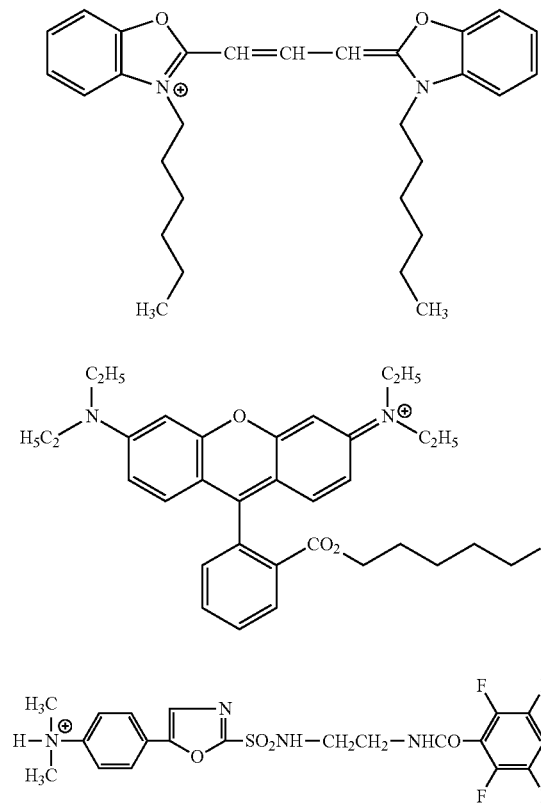

[Formula 2]

Dye 1:

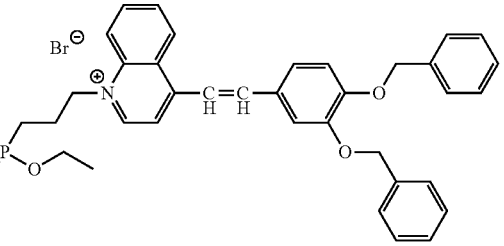

Dye 5:

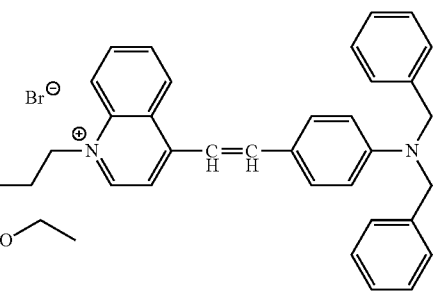

Dye 7:

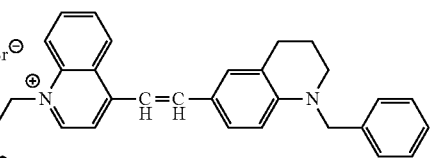

Dye 10:

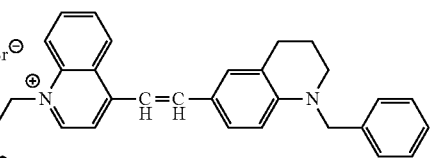

The Dye 1, 5, 7 and 10 are cationic in amphiphilic condition, and have moderate lipophilicity, and examples of the fluorescent probe 1. These dyes are described in US Patent Application Publication US2010/0068752A1, the entire disclosure of which is incorporated herein by reference. These dyes can be synthesized according to the description of the US patent application publication, but some of them are commercially available. The amphiphilic index (AI) and the hydrophobic index of the dye 1 is 4.95 and 3.77, respectively, and it has an univalent cation. The amphiphilic index (AI) and the hydrophobic index of the dye 5 is 5.11 and 4.32, respectively, and it has an univalent cation. The amphiphilic index (AI) and the hydrophobic index of the dye 7 is 4.19 and 3.29, respectively, and it has an univalent cation. The amphiphilic index (AI) and the hydrophobic index of the dye 10 is 4.25 and 5.71, respectively, and it has an univalent cation. With using the computation software named as Pallas of CompuDrug Ltd., the hydrophobic index of the dyes 1, 5, 7 and 10 were calculated by using two independent log P calculation indicators (log P(annlogp) and log P(atomic6)) and by multiplying them with a factor for being consistent with measured value and summing the resulting values as log P(combined)=0.863× log P(annlogp)+0.137×log P(atomic6). The amphiphilic indexes were calculated by removing phosphate group (P-O) from the log P(annlogp) value.

(2) As an example of substrates having a certain level of affinity to a protein localizing in the endoplasmic reticulum, for example, fluorescent labeled glibenclamide and fluorescent labeled Brefeldin A can be listed.

Glibenclamide is the compound shown by the following formula and is commercially available under the brand names: ER-Tracker (registered trademark) Green (BO-DIPY® FL glibenclamide), and ER-Tracker (registered trademark) Red (BODIPY® TR glibenclamide), which are compounds of combining fluorescent dye (BODIPY) with glibenclamide. Glibenclamide compound is known as binding to sulphonylurea receptors of ATP-sensitive K+ channels which are many in the endoplasmic reticulum and inhibiting its function, and has been used as antidiabetic drug. The dissociation constant to ATP-sensitive K+ channel of glibenclamide is 0.1-3.6 nM.

[Formula 3]

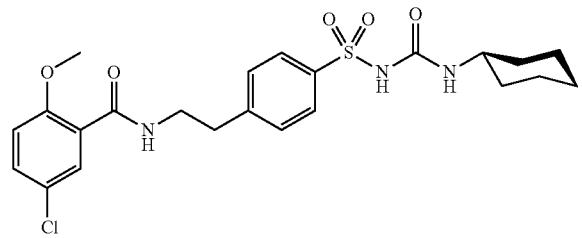

Brefeldin A is the compound shown by the following formula and is commercially available under the brand names: BODIPY-brefeldin A which is the compound of combining fluorescent dye (BODIPY) with Brefeldin A. Brefeldin A inhibits the function of the Arf1 protein which is GTP-exchanging factor acting on the vesicular transfer to Golgi body from the endoplasmic reticulum.

[Formula 4]

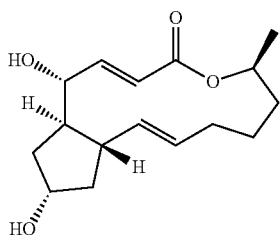

Fluorescent-Probe 2

The fluorescent probe (fluorescent probe 2) as the second embodiment of the present invention is the fluorescent probe to use for identifying or isolating plasma cells and plasmablasts and has affinity to the nuclei of cells other than plasma cells and plasmablasts higher than one to nuclei of plasma cells and plasmablasts with two times or more. By staining with the fluorescent probe 2 plasma cells and plasmablasts and cells other than plasma cells and plasmablasts can be discriminated each other. The fluorescent probe strongly stains the nuclei of other cells possibly co-existing, but has low affinity to the nuclei of plasma cells and plasmablasts. Therefore, by harvesting/removing cells which are stained stronger with the fluorescent probe 2, the concentration of plasma cells and plasmablasts in a sample can be raised. Chromosomes in the nuclei of cells other than plasma cells and plasmablasts aggregate gently, while chromosomes in the nuclei of plasma cells and plasmablasts strongly aggregate and show the heterochromatin structure. As a result, the fluorescent probe selectively staining chromosomes shows stronger staining to the nuclei of cells other than plasma cells and plasmablasts, but weak staining to the nuclei of plasma cells and plasmablasts, and thus there is difference between them.

The fluorescent probe 2 gives the fluorescent intensity for staining the nuclei of cells other than plasma cells and plasmablasts which is preferably equal to or more than 3 times, more preferably equal to or more than four times higher compared with the fluorescence intensity for staining the nuclei of plasma cells and plasmablasts. The higher the fluorescent intensity ratio is, the more efficient cells other than plasma cells and plasmablasts among a cell group containing plasma cells and plasmablasts can be identified, and as a result, cells other than plasma cells and plasmablasts can be efficiently separated and removed. As examples of cells other than plasma cells and plasmablasts, for example, T lymphocyte, B lymphocyte, macrophage, neutrophil, acidocyte, and basocyte and so on can be listed. In addition, erythrocyte and platelet are not stained with the fluorescent probe 2 because of acaryote, and thus it is difficult to discriminate them from plasma cells and plasmablasts which is hard to be stained with the fluorescent probe 2.

The fluorescent probe 2 may be any substance which has staining selectivity to cell nuclei higher than to other cell organelles and so on. This is why as long as the substance selectively staining cell nuclei the difference in fluorescent intensity can be obtained between low stainability of chromosome caused by heterochromatin structure in the cell nuclei of plasma cells and plasmablasts and stainability of chromosome in the nuclei of cells other than plasma cells and plasmablasts.

According to the present invention, the discrimination between plasma cells and plasmablasts and cells other than plasma cells and plasmablasts by using the fluorescent probe 2 of the present invention can be accomplished as below. The fluorescent probe 2 is added to cell suspension and the resulting solution is incubated at 37° C. for 30 min for staining. A suitable concentration of the fluorescent probe 2 for staining depends on the kind of the fluorescent probe, and, for example, it is 100 nM to 1 μM. After staining, cells are washed with PBS. Washed cells are subject to, for example, (1) observing the localization of the fluorescent probe in cells by using a fluorescent microscope, or (2) based on the intensity of fluorescence emitting from cells, the cells can be identified as plasma cells and plasmablasts or cells other than plasma cells and plasmablasts. The way of discriminating between plasma cells and plasmablasts and cells other than plasma cells and plasmablasts will be described in detail in the method of identifying and isolating plasma cells and plasmablasts.

Moreover, by using the method for determining the staining selectivity for the nuclei above, a substance which can be used as the fluorescent probe 2 can be screened from substances having unknown affinity to the nuclei of plasma cells and plasmablasts and the nuclei of cells other than plasma cells and plasmablasts. As examples of the plasma cells and plasmablasts and the cells other than plasma cells and plasmablasts which are used in the method for screening a substance usable as the fluorescent probe 2, for example, plasma cells and plasmablasts, T lymphocyte, B lymphocyte, macrophage, neutrophil, acidocyte, basocyte and so on can be listed. By using these cells, the screening of a substance usable as the fluorescent probe 2 can be implemented easily and conveniently. In addition, as described above erythrocyte and platelet are not suitable as cells used in the determining method of staining selectivity for the nuleci because of acanyote.

A substance usable as the fluorescent probe 2 can be screened by using plasma cells and plasmablasts which is cells having heterochromatin structure remarkably in its nuclei because it is finally differentiated and in which only specific genes are expressed in large quantity and other gene expressions are suppressed, cells capable of growth, or normal cells in which heterochromatin structure is not remarkably observed in the nuclei because of expressing various genes even if it is finally differentiated.

As an example of the fluorescent probe 2, for example, SYTO 59, SYTO 24 and so on can be listed. SYTO 59 is a Cyanine dye and is a fluorescent dye having the maximum absorption wavelength of 615 nm and the maximum emission wavelength of 650 nm when binding to DNA. SYTO 24 is a Cyanine dye and is a fluorescent dye having the maximum absorption wavelength of 490 nm and the maximum emission wavelength of 515 nm when binding to DNA. Therefore, the fluorescent probe 2 can be chosen among substances which selectively bind to DNA.

In the above SYTO 59 and SYTO 24, as those material characteristics two nitrogen atoms are connected via a polymethylene chain and each nitrogen atom forms an aromatic ring independently. At least one of the nitrogen atoms has positive electric charge as quaternary ammonium group. It has AI<8 and −5<log P(cation)<0. A substance selectively binding to DNA can be selected by suing this property as an index.

As examples of cells other than plasma cells and plasmablasts possibly co-existing with plasma cells and plasmablasts at the time of the identification or isolation of plasma cells and plasmablasts in the present invention, for example, T lymphocyte, B lymphocyte, macrophage, neutrophil, acidocyte, basocyte and so on can be listed. The endoplasmic reticulum of these cells doesn't develop compared with the endoplasmic reticulum of plasma cells and plasmablasts, and thus the fluorescent intensity stained with the fluorescent probe 1 is sufficiently low compared with the fluorescent intensity obtained from plasma cells and plasmablasts and the difference of both fluorescent intensities can be discriminated. On the contrary, the nuclei of these cells do not form heterochromatin structure and thus the fluorescent intensity stained with the fluorescent probe 2 is sufficiently high compared with the fluorescent intensity obtained from plasma cells and plasmablasts and the difference of both fluorescent intensities can be discriminated Both the fluorescent probes 1 and 2 of the present invention can be used for identifying and isolating plasma cells and plasmablasts from, for example, a lymph node tissue, a hemocyte sample or bone marrow. Specifically, cell suspension is prepared from lymph node tissue, hemocyte sample or bone marrow taken out from an animal by using a conventional method, and then the fluorescent probe 1 or 2 is added to the resulting cell suspension for cell staining. By analyzing the staining with, for example, a fluorescent microscope or a flow cytometer, cells which have high florescent intensity when stained with the fluorescent probe 1 can be assessed as candidates of plasma cells and plasmablasts, and cells which have high florescent intensity when stained with the fluorescent probe 2 can be assessed as candidates of cells other than plasma cells and plasmablasts. With the similar method using a micromanipulator equipped to a fluorescent microscope or a cell sorter, it is possible to isolate or separate plasma cells and plasmablasts or candidates thereof from the cell suspension.

<Plasma Cells and Plasmablasts Identification and Isolation Method 1>

The present invention includes the method for identifying plasma cells and plasmablasts in lymph node tissue, hemocyte sample or bone marrow, and the method for obtaining the plasma cells and plasmablasts by harvesting the cells identified by the method. The fluorescent probe 1 is used in the method for identifying plasma cells and plasmablasts in lymph node tissue, hemocyte sample or bone marrow.

Specifically, the fluorescent probe 1 is added to cells derived from lymph node tissue, hemocyte sample or bone marrow, and stains them. The lymph node tissue, hemocyte sample or bone marrow is derived from, for example, human, troglodyte, monkey, canine, cat, horse, bovine, porcine, sheep, goat, donkey, camel, Lama, alpaca, reindeer, buffalo, yak, guinea pig, rabbit, mink, mouse, rat, Mongolian gerbil, hamster, golden hamster, Armenian hamster, ferret, miniature-pig, raccoon, opossum, suncus, kangaroo, dolphin, fowl, quail or ostrich.

The lymph node tissue, hemocyte sample or bone marrow can be prepared by, for example, the followings. After more than one month from when an antibody is injected into a mouse subcutaneously or via its foot pad, an expanded lymph node tissue of the mouse is taken out. After tissues accompanying the lymph node are removed, by breaking the capsule covering the lymph node with a tweezers cells in the lymph node are dispersed into PBS solution (10 mM phosphate buffer, 120 mM NaCl, 2.7 mM KCl, pH 7.6). For the hemocyte sample, blood is obtained from an immunized animal by blood collection of heparin and the resulting blood is subject to the density gradient centrifugation to isolate mononuclear cells, which is used as hemocyte sample. For bone marrow, both ends of a thighbone taken out from the immunized animal are cut, PBS solution flows into bone marrow via an injection needle inserted into one end of the bone ends, and bone marrow cells eluted from the other end of the bone ends are collected and used as the bone marrow.

The additive amount of the fluorescent probe 1 for the lymph node tissue, hemocyte sample or bone marrow is arbitrarily determined by considering sensitivity of a detecting device, composition of cell suspension, time period for staining and so on. For example, when ER-Tracker Blue white DPX is used, the range of 100 nM-1 μM can be listed, but it does not intend to limit the present intention to this range.

By using the lymph node tissue, hemocyte sample or bone marrow stained with the fluorescent probe 1, plasma cells and plasmablasts (or cells which are highly possible to be plasma cells and plasmablasts) are identified based on its fluorescence. The method for identifying plasma cells and plasmablasts includes, as described above, (1) the method for observing the localization of the fluorescent probe in the stained cells by a fluorescent microscope, and (2) the method based on the fluorescent intensity emitted from the stained cells.

(1) With the method for observing the localization of the fluorescent probe in cells by using a fluorescent microscope in which the area of the endoplasmic reticulum in cells is strongly stained (i.e., strong fluorescence is emitted), as to one cell to be observed, the cell in which the area ratio of the area of the endoplasmic reticulum stained strongly is more than about 65% can be identified as a plasma cell and plasmablast. In addition, instead of the area ratio, as to one sell itself, when the fluorescent intensity of the whole cell is taken as 100%, the cell in which the ratio of the fluorescent intensity derived from the endoplasmic reticulum is more than about 65% can be identified as a plasma cell and plasmablast. In plasma cells and plasmablasts, the fluorescent intensity of the endoplasmic reticulum among the fluorescent intensity of the one whole cell is about 65%, and the remaining 35% of the fluorescent intensity is transferred into other cell organelles (mitochondria, Golgi body, plasma membrane, etc.).

The ratio of the fluorescence intensity of the whole cell and the fluorescence intensity from the endoplasmic reticulum can be determined as the followings, by using the method for identifying the cell endoplasmic reticulum with immunostaining of a protein localizing in the endoplasmic reticulum (immunoglobulin in plasma cells and plasmablasts) or expressing a recombinant fluorescent protein capable of migrating into the endoplasmic reticulum in cultured cells.

For example, with using the 293 cells, a recombination fluorescence protein (red) is expressed in the cultured cells. The cells are stained with the fluorescent probe 1 (e.g. ER-Tracker Blue White). With using an image analysis device of a fluorescent microscope, the fluorescent intensity of the fluorescent probe 1 covering the whole cell is measured and indicated as A, and the fluorescent intensity of the fluorescent probe 1 within the area stained with the recombinant fluorescent protein (red) (the endoplasmic reticulum) is measured and indicated as B. The fluorescent intensity B corresponds to the amount of the fluorescent probe 1 localizing in the endoplasmic reticulum. Therefore, the ratio of the fluorescent intensity B from the endoplasmic reticulum in the cell to the fluorescent intensity A from the one whole cell can be indicated as B/A×100(%). As the results of the examples, in plasma cells and plasmablasts, the intensity A of ER-tracker Blue/white for one whole cell and the fluorescent intensity B of ER-tracker Blue/white in the area stained with the immunoglobulin (green) (the endoplasmic reticulum) are measured and indicated that the value of B/A×100 is equal to or more than 65%.

(2) The identification of plasma cells and plasmablasts based on the fluorescent intensity can be implemented, for example, by a fluorescence scanner, a fluorescence microscope, a flow cytometer, a cell sorter and so on. As to the fluorescent probe 1, as described above, the fluorescent intensity obtained in plasma cells and plasmablasts is higher than the fluorescent intensity obtained in cells other than plasma cells and plasmablasts with, for example, 3 times or more, preferably 4 time or more, more preferably 5 times or more. Therefore, it is easy to identify candidates of plasma cells and plasmablasts from the cells stained with the fluorescent probe 1, based on fluorescent intensity and by using a fluorescent scanner etc., described above.

When the ratio of the fluorescent intensity as the standard for selecting candidates of plasma cells and plasmablasts (plasma cells and plasmablasts/cells other than plasma cells and plasmablasts) is set higher, the ratio of true plasma cells and plasmablasts included in the candidates of plasma cells and plasmablasts becomes higher. However, when plasma cells and plasmablast which have higher fluorescent intensity than cells other than plasma cells and plasmablasts but have only the relatively low fluorescent intensity below the fluorescent intensity ratio as the standard, it is possible to exclude them. Therefore, it is preferable to choose a fluorescent intensity ratio as standard for selecting candidates of plasma cells and plasmablasts with considering the properties of plasma cells and plasmablasts contained in lymph node tissue or hemocyte sample as a sample, particularly the development of its endoplasmic reticulum.

The method of the present invention preferably further harvests (sorts) candidates of plasma cells and plasmablasts identified by the above method. The harvest of the identified cells can be conducted by, for example, the sort of a cell sorter. The candidates of plasma cells and plasmablasts which are identified or determined as plasma cells and plasmablasts (or cells which are highly possible to be plasma cells and plasmablasts) based on the fluorescence are sorted by a cell sorter.

<Plasma Cells and Plasmablasts Identification and Isolation Method 2>

The present invention includes the method for identifying plasma cells and plasmablasts in lymph node tissue, hemocyte sample or bone marrow, and the method for obtaining the plasma cells and plasmablasts by harvesting the cells identified by the identification method. The fluorescent probe 2 is used in the method for identifying plasma cells and plasmablasts in lymph node tissue, hemocyte sample or bone marrow.

Moreover, the present invention includes the method for preparing plasma cells and plasmablasts which includes: staining the cells prepared by the plasma cells and plasmablasts identification and isolation method 1 described above with the fluorescent probe 2; then identifying cells other than plasma cells and plasmablasts based on the fluorescent intensity in the sample; removing the cells identified; and harvesting the remaining cells as plasma cells and plasmablasts. However, it is possible that the method of the present invention for identifying and isolating plasma cells and plasmablasts by using the fluorescent probe 2 is applied to a sample prepared from lymph node tissue, hemocyte sample or bone marrow and then the method of the present invention for identifying and isolating plasma cells and plasmablasts by using the fluorescent probe 1 is applied.

The method for identifying plasma cells and plasmablasts includes, as the same as the plasma cells and plasmablasts identification and isolation method 1, (1) the method for observing the localization of the fluorescent probe in the stained cells by a fluorescent microscope, and (2) the method based on the fluorescent intensity emitted from the stained cells.

The condition of staining cells with the fluorescent prove, the observation of localization of the fluorescent probe and the measurement of the fluorescent intensity are the same as the plasma cells and plasmablasts identification and isolation method 1 described above. However, the fluorescent probe 2 selectively stains cell nuclei, and in lymph cells other than plasma cells and plasmablasts, such as T lymphocyte, when observing the localization of the fluorescent probe in cells by using a fluorescent microscope, if the fluorescent intensity of the whole cell is taken as 100%, the ratio of the fluorescent intensity of cell nuclei is equal to or more than about 70%.

In the case of the fluorescent probe 2, it is possible to identify the nuclei by using cultured cells as the same as the fluorescent probe 1. That is, by using immunostaining of a protein localizing in the nuclei, expressing of a recombinant fluorescent protein capable of migrating into the nuclei, and staining with a known fluorescent dye capable of staining the nuclei (Hoechst 33342, etc.) and so on, it is possible to identify the nuclei of cultures cells. For example, 293 cells are co-stained with Hoechst 33342 (blue) and the fluorescent probe 2, and by using an image analysis device of a fluorescent microscope, the intensity A of the fluorescent probe 2 occupying the whole cell and the fluorescent intensity B of the fluorescent probe 2 in the area (nuclei) stained with Hoechst 33342 are measured. The fluorescent intensity B indicates the amount of the fluorescent probe 2 localizing in the nuclei. Therefore, from the formula B/A×100, the ratio (%) of the fluorescent probe 2 staining the cell nuclei is determined.

Specifically, the fluorescent probe 2 is added to and stains a sample prepared from lymph node tissue, hemocyte sample or bone marrow, or candidates of plasma cells and plasmablasts prepared by the plasma cells and plasmablasts identification and isolation method 1 described above. The amount of the fluorescent probe 2 added to cells is arbitrary determined by considering sensitivity of a detector, composition of cell suspension, time period for staining and so on, but it may be the range of 10 nM to 5 µM. However, it is not intended to limit the invention to the range.

The fluorescent intensity of the fluorescent probe 2 obtained from staining the nuclei of cells other than plasma cells and plasmablasts, compared to the fluorescent intensity obtained from staining the nuclei of plasma cells and plasmablasts, is high sufficient to discriminate them, for example, with two times higher or more. Therefore, it is possible to effectively identify cells other than plasma cells and plasmablasts among a cell group containing cells other than plasma cells and plasmablasts in addition to plasma cells and plasmablasts.

When the ratio of the fluorescent intensity as the standard for selecting candidates of plasma cells and plasmablasts among a cell group containing cells other than plasma cells and plasmablasts in addition to plasma cells and plasmablasts (cells other than plasma cells and plasmablasts/ plasma cells and plasmablasts) is set higher, the ratio of contamination of cells other than plasma cells and plasmablasts into the plasma cells and plasmablasts becomes lower. However, when plasma cells and plasmablasts have the lower fluorescent intensity than cells other than plasma cells and plasmablasts but have relatively high fluorescent intensity above the fluorescent intensity ratio as the standard, it is possible to exclude them. However, if the fluorescent intensity ratio as the standard above is set too low, the contamination ratio of cells other than plasma cells and plasmablasts contained into plasma cells and plasmablasts becomes higher. Therefore, it is preferable to choose a fluorescent intensity ratio as the standard for selecting candidates of plasma cells and plasmablasts with considering the properties of plasma cells and plasmablasts contained in lymph node tissue or hemocyte sample as a sample, particularly the development of the nuclei having car spoke like structure. In the comparison of the case that the fluorescent intensity ratio as the standard is set, for example, as 2 times and cells are discriminated to the case that it set as 4 times and cells are discriminated, the case of setting 4 times has high possibility to remove cells other than plasma cells and plasmablasts which are contaminated into plasma cells and plasmablasts. However, it should be considered that the higher the fluorescent intensity ratio is set, the higher the possibility of removing plasma cells and plasmablasts contaminated into plasma cells and plasmablasts is.

With using cells stained with the fluorescent probe 2, cells other than plasma cells and plasmablasts (or cells having low possibility to be plasma cells and plasmablasts) are identified based on the fluorescence. The identification of cells other than plasma cells and plasmablasts based on the fluorescence is implemented, for example, as the same as the fluorescent probe 1 described above.

The method of the present invention preferably includes: further harvesting (sorting) cells identified by the above described method, and separating plasma cells and plasmablasts (or cells having high possibility to be plasma cells and plasmablasts) from cells other than plasma cells and plasmablasts (or cells having low possibility to be plasma cells and plasmablasts). The preparation of the identified cells is conducted by cell sorter preparation.

The plasma cells and plasmablasts identification and isolation methods 1 and 2 using the fluorescent probe described above according to the present invention can be combined with a method of using an antibody against known cell surface antigen. By combining with the method of using an antibody against known cell surface antigen, depending on kind or property of the antibody it may be a case that identification and isolation of plasma cells and plasmablasts is performed with high precision.

As the method of using an antibody against known cell surface antigen, for example, the following method can be listed. After one month or more from injecting an antigen into a mouse subcutaneously or via its foot pad, cells obtained from an expanded lymph node tissue of the mouse and CD138 which is one of cell surface antigens of plasma cells and plasmablasts are stained with allophycocyanin labeled anti CD138 antibody, and then the cells and the endoplasmic reticulum are stained with the fluorescent probe 1 described above. It makes possible to select plasma cells and plasmablasts among CD138 positive cells.

EXAMPLES

Hereinafter, the present invention is explained in detail with the following examples. However, it is not intended to limit the present invention to the following examples.
Experimental Method
1. Concentration of Plasma Cells and Plasmablasts from Mouse Lymph Node Fifty µg of green fluorescent protein (GFP) derived from *Aequorea victoria* emulsified by adding the same volume of adjuvant (Titer Max Gold) was injected into a foot pad of an ICR female mouse (6 weeks old). After 4 weeks from the immunization, the lymph node below knee was taken out, and cell suspension was prepared by using it. The concentration of plasma cells and plasmablasts from the cell suspension was conducted by the magnetic bead cell separation method using antibodies against cell surface markers (Miltenyi Biotech, Plasma Cell Isolation Kit). The cell group having CD49b negative, CD45R negative and CD138 positive was obtained.

2. Identification of Plasma Cells and Plasmablasts Using Fluorescent Probe
2-1. Endoplasmic Reticulum Staining Cell staining was conducted by using ER-Tracker (registered trademark) Blue-White DPX/lipid (Invitrogen Inc.) as the probe having affinity to the endoplasmic reticulum. In other words, after cells were suspended in 1 ml of PRMI 1640 medium, 1 µl of ER-Tracker (registered trademark) Blue-White DPX/lipid solution was added to and then was incubated for 15 minutes at 37° C. under light shielding to give the fluorescent probe incorporation. Then, cells were collected by centrifugation of 1,000 rpm for 5 min, and suspended in PBS solution (10 mM phosphate buffer, 120 mM NaCl, 2.7 mM KCl, pH 7.6). For fluorescent microscope observations, an appropriate amount of the cell suspension was plated on a culture dish coated with polylysine, after attached to the bottom of the culture dish, cells were fixed with 4% formalin PBS solution for 5 min at room temperature, and the resulting staining images were captured with the Olympus BX51 fluorescence microscope. The excitation and the fluorescence detection were performed by using a WU filter.

2-2. Nuclei Staining

Cell staining with SYTO (registered trademark) 59 (Invitrogen Inc.) as the fluorescent probe having affinity to euchromatin was conducted. In other words, after cells were suspended in 1 ml of PRMI 1640 medium, 1 µl of SYTO (registered trademark) 59 solution was added to and then was incubated for 15 minutes at 37° C. under light shielding to give the fluorescent probe incorporation. Then, cells were collected by centrifugation of 1,000 rpm for 5 min, and suspended in PBS solution. The fluorescent microscope observations were conducted as the same method described above. The excitation and the fluorescence detection were performed by using a WIG filter.

2-3. Staining of Endoplasmic Reticulum and Nuclei

The double staining of the endoplasmic reticulum and the nuclei of cells were conducted by the nuclei staining with SYTO (registered trademark) 59 according to the 2-2 method, followed by the staining with ER-Tracker (registered trademark) Blue-White DPX/lipid according to the 2-1 method.

3. Preparation and Isolation of Plasma Cells and Plasmablasts by Cell Sorter

The cell suspension prepared from GFP immunized mouse was stained with SYTO (registered trademark) 59 and ER-Tracker (registered trademark) Blue-White DPX/lipid according to the method described above, and were prepared with PBS solution to give the final cell concentration of about $1-5 \times 10^6$/ml. The separation of plasma cells and plasmablasts was conducted by using the JSAN cell sorter (Bay Bioscience Inc.) and detected SYTO (registered trademark) 59 signal by the FL3 channel and ER-Tracker (registered trademark) Blue-White DPX/lipid signal by the FL7 channel. The gate setting to separate plasma cells and plasmablasts from other cells was 4 times of the average signal at the FL7 channel gate, and 0.5 times of the average signal at the FL3 channel gate.

4. Cellular Immunoglobulin Staining

The cell group obtained by the magnetic bead cell separation method or the cells prepared and isolated by a cell sorter was immobilized on the bottom of a culture dish according to the method described in 2-1, and the staining images were captured. Then, after cell membrane was solubilized by PBS solution including 0.1% TritonX-100, cell staining was conducted by using Alexafluor488 labeled anti-mouse immunoglobulin (Invitrogen) and the staining images were captured.

The Experimental Results

Example 1

Identification of Plasma Cells and Plasmablasts by Using Fluorescent Proves Staining Endoplasmic Reticulum The cell group, which was CD49b negative, CD45R negative and CD138 positive, was obtained from the GFP immunized mouse lymph node according to the method described in the experimental method 1. These cells were stained with ER-Tracker (registered trademark) Blue-White DPX/lipid, and were subject to the fluorescence microscope observation. The result is shown in the FIG. 1. About 20% of cells emitted strong fluorescence with this probe, and these cells had the strongly stained area of the developed endoplasmic reticulum throughout cellular cytoplasm. Most of the remaining cells emitted weak fluorescence, and these cells had cell membrane area and small size of endoplasmic reticulum both of which were weakly stained. The fluorescent intensity ratio of cells emitting strong fluorescence to the remaining cells emitting weak fluorescence was about 5:1. In order to clarify whether the cells strongly stained with the probe is plasma cells and plasmablasts, the detection of immunoglobulin existing in cells according to the experimental method 4 was conducted. The results showed that most of cells having strong positive of the probe were plasma cells and plasmablasts expressing mouse IgG. From the above results, it has been proven that by using the fluorescent probe staining the endoplasmic reticulum plasma cells and plasmablasts can be identified easily and conveniently.

Example 2

Figure 2:
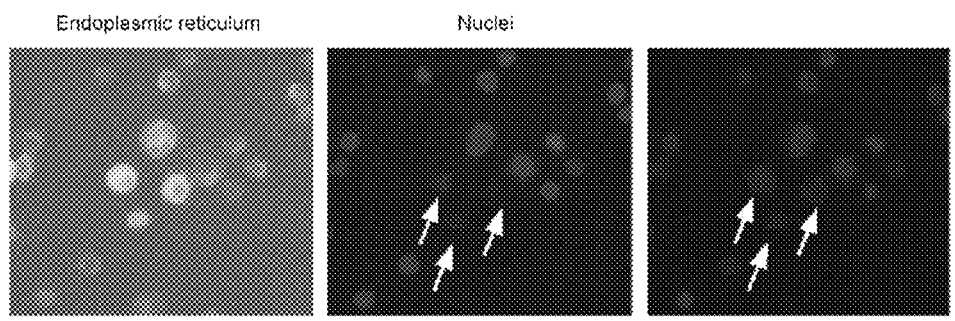
FIG. 2 shows the result of identification test of plasma cells and plasmablasts with the euchromatin affinity fluorescent probe which selectively stains the endoplasmic reticulum in Example 2. The result is the fluorescent microscope observation of the cell group of CD49b negative, CD45R negative and CD138 positive by staining with SYTO (registered trademark) 59 and ER-Tracker (registered trademark) Blue-White DPX/lipid.

Identification of Plasma Cells and Plasmablasts Using Fluorescent Probe Having Affinity to Endoplasmic Reticulum and Fluorescent Probes Having Affinity to Euchromatin The cell group, which was CD49b negative, CD45R negative and CD138 positive, obtained by the method described in the experimental method 1 was subject to the cell staining with SYTO (registered trademark) 59 and ER-Tracker (registered trademark) Blue-White DPX/lipid according to the method described in the experimental methods 2-2 and 2-3. The result is shown in the FIG. 2. Most of cells strongly stained with ER-Tracker (registered trademark) Blue-White DPX/lipid were weakly stained with SYTO (registered trademark) 59. The ratio of the fluorescent intensity of SYTO59 between cells having strongly stained cell nuclei and cells having weak stained cell nuclei was about 4:1.

The above results of cell staining were well corresponded to the specific morphology of plasma cells and plasmablasts (developed endoplasmic reticulum and car spoke like nuclei having an abundance of heterochromatin), and thus it is proven that with combining two kinds of probes: a fluorescent prove having affinity to the endoplasmic reticulum and a fluorescent probe having affinity to euchromatin, it is possible to identify plasma cells and plasmablasts with higher precision.

Example 3

The ratio of plasma cells and plasmablasts among a lymph node cell group is equal to or less than about 0.1%. In order to obtain a high purity of plasma cells and plasmablasts from the cell group without cell surface antibodies, the inventors tried the separation and isolation of plasma cells and plasmablasts using the fluorescent probe described above and a cell sorter. Cell suspension prepared from the GFP immunized mouse lymph node was used and subject to the double staining of the endoplasmic reticulum and the nuclei according to the experimental method 2-3, and an experiment was conducted according to the preparation method of plasma cells and plasmablasts using a cell sorter described in the experimental method 3.

Figure 3:
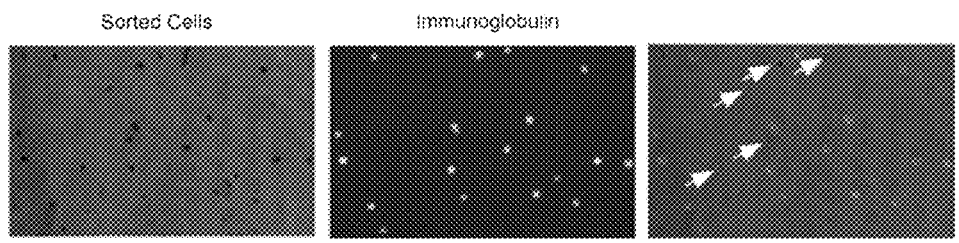
FIG. 3 shows the detection result of immunoglobulin existing in the cell group of Blue-White DPX/lipid strong positive and SYTO (registered trademark) weak positive which is sorted by a cell sorter in Example 3.

The cell group which was Blue-White DPX/lipid strong positive and SYTO (registered trademark) 59 weak negative were sorted by a cell sorter. For the sorted cells which were Blue-White DPX/lipid strong positive and SYTO (registered trademark) 59 weak negative, in order to clarify the occupying ratio of plasma cells and plasmablasts the detection of immunoglobulin existing in cells was conducted according to the method described in the experimental method 4. The result is shown in the FIG. 3. The result proved that about 75% of the obtained cells were plasma cells and plasmablasts (FIG. 3: the arrows show immunoglobulin positive cells). The above results proved that by conducting the fluorescent probe staining utilizing the specific morphology of plasma cells and plasmablasts it was possible to isolate plasma cells and plasmablasts, which is much superior to the conventional isolation method of plasma cells and plasmablasts depending cell surface antibodies.

Example 4

Identification of Rat Plasma Cells

Experimental Method

A Wistar rat (female, 6 weeks old) was used as an immune animal. An egg albumin was used as an antigen. The rat was immunized by injecting 50 μg of egg albumin intramuscularly into both sides of the root of its tail for three times every other month. After the completion of immunization, the iliac lymph node was taken out from the rat. The cells were suspended in PBS containing 0.5% bovine serum albumin and then suspended in DMEM medium, and was subject to the endoplasmic reticulum staining by adding ER-Tracker (1 μM) and storing for 5 min at room temperature. After washing cells with PBS, the plasma cell fraction was isolated as ER-Tracker strong positive cells by a cell sorter.

Results

Figure 4:
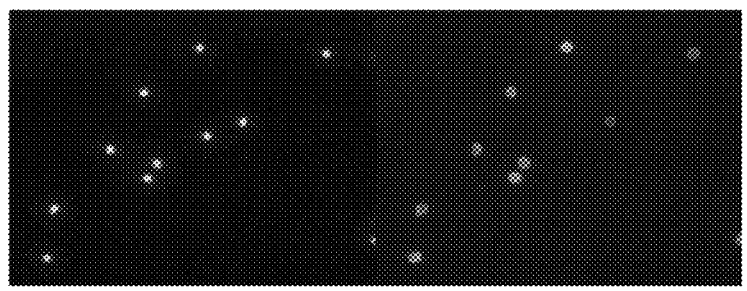
FIG. 4 shows the detection result of immunoglobulin existing in the rat cell group of ER-Tracker (registered trademark) Blue-White DPX/lipid strong positive which is sorted by a cell sorter in Example 4.

In the rat plasma cells isolated by using ER-Tracker, in order to determine the occupying ratio of plasma cells and plasmablasts the detection of immunoglobulin existing in cells was conducted according to the method described in the experimental method 4. The result is shown in the FIG. 4. The left is the nuclei staining with Hoechst 33342. The right is the cell interior immunoglobulin stained with FITC labeled anti-rat antibody. Since most of cells have immunoglobulin in the cell interior, it is clear that the sorted cells were plasma cells.

Example 5

Identification of Plasma Cells of Guinea Pig

Experimental Method

A Hartley guinea pig (female, 6 weeks old) was used as an immune animal. An egg albumin was used as an antigen. The guinea pig was immunized by injecting 50 μg of egg albumin intramuscularly into both sides of the root of its tail for three times every other month. After the completion of immunization, the iliac lymph node was taken out from the guinea pig. The cells were suspended in PBS containing 0.5% bovine serum albumin and then suspended in DMEM medium, and was subject to the endoplasmic reticulum staining by adding ER-Tracker (1 μM) and storing for 5 min at room temperature. After washing cells with PBS, the plasma cell fraction was isolated as ER-Tracker strong positive cells by a cell sorter.

Results

Figure 5:
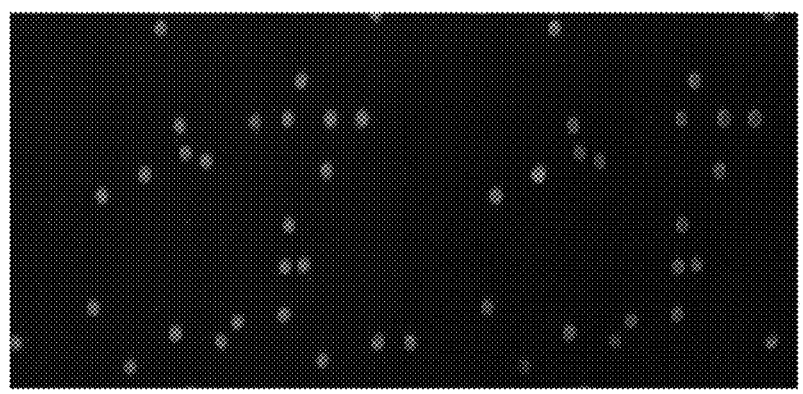
FIG. 5 shows the detection result of immunoglobulin existing in the guinea pig cell group of ER-Tracker (registered trademark) Blue-White DPX/lipid strong positive which is sorted by a cell sorter in Example 5.

In the guinea pig plasma cells isolated by using ER-Tracker, in order to determine the occupying ratio of plasma cells and plasmablasts the detection of immunoglobulin existing in cells was conducted according to the method described in the experimental method 4. The result is shown in the FIG. 5. The left is the endoplasmic reticulum staining using the fluorescent probe having affinity to the endoplasmic reticulum (ER-IDTM, the ENZO Life Sciences Inc.). The right is the cell interior immunoglobulin stained with FITC labeled anti-rat antibody. Since most of cells have the developed endoplasmic reticulum and immunoglobulin in the cell interior, it is clear that the sorted cells were plasma cells.

The above results have proven that by using the present invention high purity of plasma cells and plasmablasts can be isolated regardless of animal species.

INDUSTRIAL APPLICABILITY

The present invention is available to develop antibody drug and diagnostic drug and so on.

The invention claimed is:

1. A method for preparing plasma cell(s) and plasmablast(s) comprising:
    immunizing an animal with an antigen;
    taking lymph node tissue, hemocyte preparation and/or bone marrow from the animal;
    deriving cells, including the plasma cell(s) and plasmablast(s), from the lymph node tissue, hemocyte preparation or bone marrow;
    staining the cells derived from the lymph node tissue, hemocyte preparation or bone marrow with a first fluorescent probe having a staining selectivity,
    wherein the staining selectivity of the first fluorescent probe is higher for the endoplasmic reticulum in the plasma cell(s) and plasmablast(s) than for a cell structure other than the endoplasmic reticulum, and
    wherein the stained plasma cell(s) and plasmablast(s) are distinguishable from derived cells other than the plasma cell(s) and plasmablast(s);
    identifying cells within the stained cells as plasma cell(s) and/or plasmablast(s) based on a fluorescent intensity ratio defined as fluorescent intensity of plasma cell(s) and plasmablast(s) divided by fluorescent intensity of cells other than plasma cell(s) and plasmablast(s); wherein the fluorescent intensity ratio is equal to or more than 3; and
    harvesting the identified plasma cell(s) and/or plasmablast(s) from among the cells with a cell sorter by means of the fluorescent intensity ratio.

2. The method according to claim 1, wherein the harvested plasma cell(s) and/or plasmablast(s) are stained by a second fluorescent probe, wherein the staining selectivity of the second fluorescent probe is higher for cell nuclei in the plasma cell(s) and plasmablast(s) than for cell structures other than the endoplasmic reticulum and the cell nuclei, and
    wherein by staining with the second fluorescent probe, the plasma cell(s) and plasmablast(s) are distinguished from cells other than plasma cell(s) and plasmablast(s), by identifying fluorescence-emitting plasma cell(s) and plasmablast(s), and harvesting the identified plasma cell(s) and/or plasmablast(s).

3. The method according to claim 1, wherein the first fluorescent probe is selected from the group consisting of a substance which is amphiphilic and cationic and has moderate lipophilicity and a substance which has affinity to a protein localized in endoplasmic reticulum above a certain degree;
    wherein being amphiphilic is defined as the amphiphilic index (AI) of the first fluorescent probe is in the range $+6>AI>0$, the moderate lipophilicity is defined as the hydrophobic index (log P) of the first fluorescent probe is in the range $+6>\log P>0$, and the affinity above a certain degree is defined by the dissociation constant of the first fluorescent probe to the protein localized in the endoplasmic reticulum, is in the range of 0.1 μM to 0.1 nM.

4. The method according to claim 1, wherein the cell structure other than endoplasmic reticulum includes at least one of plasma-membrane, mitochondria, Golgi body, lysosome, peroxisome, nucleus, centrosome, cytoplasm, phagosome, endosome, or aggresome.

5. The method according to claim 1, wherein the first fluorescent probe includes at least one of fluorescent labeled glibenclamide, fluorescent labeled brefeldin A and a fluorescent protein that localizes to the endoplasmic reticulum.

6. The method according to claim 2, wherein the second fluorescent probe is a substance having an affinity to DNA.

7. The method according to claim 2, wherein the second fluorescent probe has a chemical structure including two nitrogen atoms connected, directly or indirectly, via a polymethylene chain, each respective nitrogen atom of the two nitrogen atoms forms a part of a respective independent aromatic ring, and at least one nitrogen atom of the two nitrogen atoms has positive electric charge as quaternary ammonium.

8. The method according to claim 7, wherein the second fluorescent probe has an amphiphilicity index (AI) of <8, and a hydrophobic index (log P) of $-5<\log P(\text{cation})<0$.

9. The method according to claim 2, wherein the harvesting of the derived cell(s) other than the plasma cell(s) and plasmablast(s) and the harvesting of the remaining cell(s) are performed by sort of a cell sorter.

10. The method according to claim 1, wherein the lymph node tissue, hemocyte preparation or bone marrow is derived from one of a human, anthropoid, monkey, canine, cat, horse, bovine, porcine, sheep, donkey, camel, llama, alpaca, reindeer, buffalo, yak, guinea pig, rabbit, mink, mouse, rat, mongolian gerbil, hamster, golden hamster, armenian hamster, ferret, miniature pig, raccoon, opossum, suncus, kangaroo, dolphin, fowl, quail or ostrich.

* * * * *